United States Patent [19]
de Juan, Jr.

[11] Patent Number: 6,092,898
[45] Date of Patent: Jul. 25, 2000

[54] SURGICAL CONTACT LENS, METHODS FOR VIEWING THE INTERIOR OF AN EYE AND METHODS FOR MANUFACTURING SUCH LENSES

[75] Inventor: Eugene de Juan, Jr., Phoenix, Md.

[73] Assignee: Johns Hopkins University, Baltimore, Md.

[21] Appl. No.: 09/186,324

[22] Filed: Jul. 6, 1998

[51] Int. Cl.$^7$ ............................... G02C 7/04; A61B 3/00
[52] U.S. Cl. ...................... 351/160 R; 351/177; 351/219
[58] Field of Search ........................... 351/160 R, 160 H, 351/161–167, 177, 219; 623/6, 6.11, 6.56, 6.62

[56] References Cited

U.S. PATENT DOCUMENTS

| | | | |
|---|---|---|---|
| 3,876,450 | 4/1975 | Tanner | 351/166 |
| 4,079,470 | 3/1978 | Deeg et al. | 351/159 |
| 4,521,088 | 6/1985 | Masom | 359/507 |
| 4,695,697 | 9/1987 | Kosa | 219/121.83 |
| 5,133,750 | 7/1992 | Momose et al. | 623/6 |
| 5,264,465 | 11/1993 | Futamura et al. | 523/106 |
| 5,489,301 | 2/1996 | Barber | 623/5 |
| 5,523,810 | 6/1996 | Volk | 351/219 |
| 5,555,131 | 9/1996 | Horton | 359/661 |
| 5,573,544 | 11/1996 | Simon et al. | 606/151 |

OTHER PUBLICATIONS

International Search Report dated Sep. 8, 1999.

*Primary Examiner*—Georgia Epps
*Assistant Examiner*—Jordan M. Schwartz
*Attorney, Agent, or Firm*—Peter F. Corless; William J. Daley, Jr.; Christine C. O'Day

[57] ABSTRACT

The invention provides a sapphire surgical contact lens to view interior structures and regions of an eye as well as methods for making and using such a surgical contact lens. The surgical contact lens includes a transparent member comprising sapphire and having a first and a second surface. The first surface may be configured in a variety of ways, e.g. with a geometry that complements the curvature of a cornea, in particular the cornea's radius of curvature. More particularly the first surface is suitably configured so as to be generally concave so as to form a portion of a spherical surface. The second surface is configured with a geometry that, in cooperation with the first surface geometry, yields a given optical configuration for viewing the interior of the eye. In a preferred aspect, the transparent member is made from a single crystal of sapphire.

24 Claims, 2 Drawing Sheets

SURGICAL CONTACT LENS, METHODS FOR VIEWING THE INTERIOR OF AN EYE AND METHODS FOR MANUFACTURING SUCH LENSES

FIELD OF INVENTION

The present invention relates to surgical contact lenses useful to view the interior of an eye and more particularly to surgical contact lenses that are made from a natural or synthetic sapphire, and methods related thereto for making and using such lenses.

BACKGROUND OF THE INVENTION

To aid in viewing the interior structures and regions of the eye when performing intraocular surgery, such as for example vitreo retinal surgery, one or more surgical contact lenses have been fitted into a lens ring that is sutured in place and spans the cornea. A cushion of transparent Healon or similar material is typically applied to the anterior surface of the eye to prevent corneal abrasion and to enhance optical clarity. These surgical lenses have been fabricated from various types of glasses.

During a given surgical procedure, such current surgical contact lenses typically are removed from the lens ring and replaced several times using forceps. For example, a lens having one optical arrangement or configuration may be replaced with a lens having a different optical arrangement. As a result, these glass contact lenses often quickly degrade in optical quality because of scratches or chips resulting from manipulation with the forceps or other instruments.

Additionally, to attempt to reuse current lenses, efforts are made to clean and sterilize the lenses between surgical procedures. However, such cleaning and sterilization often results in scratching or other optical degradation.

Consequently, current lenses are often used only in a limited number of several surgical procedures before being discarded due to optical degradation. Of course, such limited use results in significant costs and waste. Also, special care is generally exercised when handling current lenses during a surgical procedure or when cleaning to minimize scratching or other optical damage. Such requisite careful handling is also clearly problematic and complicates surgical and cleaning procedures.

It thus would be desirable to have improved surgical contact lenses that were sufficiently robust to resist degradation from typical handling and cleaning procedures. It would be particularly desirable to have improved surgical contact lenses that were sufficiently robust to enable repeated use of lenses, thereby reducing costs and waste.

SUMMARY OF THE INVENTION

We have now produced new surgical contact lenses that are substantially more durable than prior lenses. The lenses of the invention are highly resistant to scratching, chipping or other degradation during typical surgical use as well as during cleaning and sterilization procedures. Consequently, surgical lenses of the invention can be reused for multiple surgical procedures, providing substantial cost and waste savings.

More particularly, the present invention provides surgical contact lenses that are formed from or otherwise comprise a transparent natural or synthetic sapphire member.

Lenses of the invention are suitably configured so a user (e.g. an ophthalmic surgeon) can view the interior of an eye such as the retina or the detached portions of the retina.

Thus, for example, the transparent member of lenses of the invention suitably comprises first and second surfaces, wherein the first surface has a shape that complements the radius of curvature of a cornea, and the second surface has a shape that, in cooperation with the first surface shape, yields a given optical configuration for viewing the interior of the eye. In particular, the first surface of the transparent member is typically generally convex and forms a portion of the surface of a sphere. The second surface of the transparent member may suitably have a variety of shapes, e.g. offset-concave. prism-concave, asymmetric-concave, symmetric-concave, prism or a planar geometric configuration. Such a surgical contact lens, when disposed proximate to and spanning the cornea allows a medical practitioner to view the interior of the eye by looking through transparent member's second surface.

Lenses of the invention also may be employed at a spaced distance from a patient's eye, e.g. in a hand-held viewing device. In such arrangements, the patient's eye may be suitably infused with fluid as desired. Also, in such a spaced arrangement, the lens first surface need not directly complement the radius of curvature of the underlying cornea.

In specific embodiments, the transparent lens member is made from a single sapphire block and configured to complement the shape and size of a lens ring that is typically sutured in place and in which the surgical contact lens is fitted for viewing purposes. The transparent member also may be formed so that the thickness between the member's first and second surfaces is about 2 mm or less, e.g. about 1.5 mm or 1.0 mm.

In another aspect, the invention provides methods for viewing the interior structure and regions of the eye using a sapphire surgical contact lens as described above. Preferred methods include removably disposing the surgical contact lens on or proximate to a patient's eye so the first surface is proximate to the cornea such that a user (e.g., surgeon) looking through the lens second surface can view the eye's interior. In a more specific aspect, a plurality of surgical contact lenses are provided, each surgical contact lens having a different second surface shape; one of the plurality of surgical contact lenses is selected for use; and the selected lens is removably disposed proximate the cornea. A lens ring may be sutured to a patient's eye to span the cornea and a surgical contact lens is removably fitted within the lens ring, either before or after the lens ring has been affixed by sutures. A viewing device also can be employed that includes one or more sapphire lenses of the invention, with the lenses suitably affixed to the device in a permanent manner such as by a glue, or alternatively the one or more lenses may be releasably attached such as by fitting within a groove system of the device or the like.

A further aspect of the invention features methods for making sapphire surgical contact lenses by machining a block of sapphire to yield a transparent member having at least first and a second surfaces as described above, i.e. the first surface has a shape that complements the radius of curvature of a cornea and the second surface is configured with a geometry that, in cooperation with the first surface geometry, yields a given optical configuration. After machining, the produced member suitably is polished to provide a sapphire surgical contact lens having a given optical characteristic.

The invention also provides device kits, which preferably comprise one or more of the described lenses, preferably packaged in sterile condition.

Other aspects and embodiments of the invention are discussed below.

DETAILED DESCRIPTION OF THE INVENTION

Figure 1:
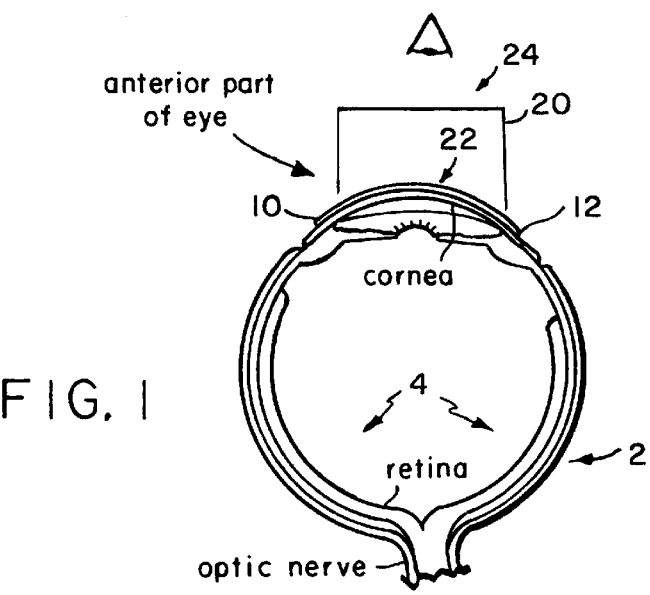
FIG. 1 is a schematic view of a sapphire surgical contact lens of the invention disposed on an eye.

Referring now to the various Figures wherein like reference characters refer to like parts, FIG. 1 shows a surgical contact lens 20 of the invention disposed on patient's eye 2 whereby medical practitioner 3 can view the interior surfaces 4 and regions of the patient eye 2. Surgical contact lens 20 is fitted into a lens ring 10 that is typically sutured to the eye 2 so the lens ring and surgical contact lens are proximate to and substantially span the cornea. Additionally, a transparent cushion 12 of Healon or similar material is suitably applied over the anterior surface of the eye 2 and between the surgical contact lens 20 and the patient eye 2 to avoid corneal abrasion or other injury.

As discussed above, the surgical contact lens 20 is made from transparent natural or synthetic sapphire ($Al_2O_3$). By stating herein that sapphire or a sapphire element is transparent, it is meant that the material or element is sufficiently transparent for its intended surgical use, i.e. whereby a medical practitioner can view through the material or element to the interior of a patient's eye. Accordingly, transparent sapphire or sapphire element need not transmit 100 percent of visible light. Rather, the material or element should transmit a sufficient amount of light to enable surgical use as desired. Such a sufficient amount of light may be e.g. transmission of about 50% or more of visible light, or more typically transmission of about 60%, 70%, 80%, 90% or more of visible light.

Additionally, references herein to sapphire are inclusive of both natural (corundum) and synthetic forms of $Al_2O_3$ that are sufficiently transparent and durable for use as a surgical contact lens as described herein. The preferred material is a standard natural or synthetic sapphire, e.g. having a density of about 3.98, Mohs hardness about 9.0; and melt point of about 2040° C. Also, it is preferred that a sapphire lens be formed of about 100% of a sapphire material, although composites also could be employed. For example, a lens of the invention could include a thin glass inner member encased by sapphire. Preferably, in such composites, the entire outer exposed surface of the lens will be sapphire, or a majority of the outer surface will be sapphire, e.g. 90%, 95% or 98% or more of the exposed outer surface area will be sapphire. In such composites, generally about 30% or 40% or more of the total volume of such a composite lens will be sapphire, more typically, about 50%, 60% or 70% or more of the total volume of such a composite lens will be sapphire, more preferably about 80%, 85%, 90% or 95% of the total volume of such a composite lens will be sapphire.

It is has been found that sapphire lenses of the invention are substantially more robust and durable than glasses currently used to fabricate current surgical contact lenses. It thus has been found that sapphire contact lenses of the invention are significantly more resistant to scratching and chipping during normal surgical use and subsequent cleaning relative to current glass lenses. Additionally, sapphire lenses of the invention are biologically stable, are extremely inert and highly resistant to discoloration and staining. Further, sapphire lenses of the invention have the ability to be sterilized by autoclaving. Thus, in contrast to prior surgical lenses, no special care needs to be taken to prevent scratching when using a surgical contact lens of the invention, or to minimize discoloration or staining of the lens.

Figure 2D:
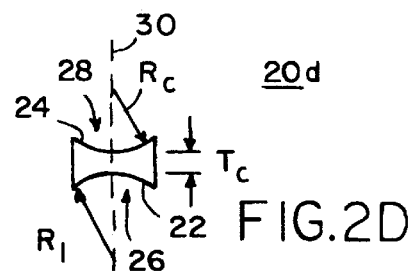
FIGS. 2A–2G are cross-sectional side views of various exemplary lens geometries of surgical contact lenses of the present invention.

It also has been found that because of the comparatively high strength, the center thickness (i.e. the distance between two opposing center surfaces shown as $T_c$ in FIG. 2D) of a sapphire lens of the invention can be substantially less than required for current glass surgical lenses. In particular, as discussed above, the center thickness of sapphire lenses of the invention suitably can be about 2 mm or less, even about 1.5 mm or less. In contrast, a typical glass lens would have a center thickness that would be about 1.5 times thicker than a surgical contact lens of the present invention.

It also has been found that the sapphire lenses of the invention exhibit excellent optical properties for use in surgery. For example, sapphire lenses of the invention have high optical transmission, from the near ultraviolet (150 nm) to the far infrared. Thus, in surgery, a surgical contact lens 20 made from sapphire can be used in an essentially identical manner as conventional lenses. Also, sapphire has a higher refractive index than the glass that has been used for prior surgical contact lenses. As a result, a sapphire lens of the present invention will have a wider angle of view relative to conventional glass surgical contact lenses having the same optical geometry or arrangement. That provides the substantial advantage of providing increased area of the interior surfaces 4 or regions of the eye that will be visible to a medical practitioner.

Suitable forms of sapphire for manufacture of lenses of the invention are readily available. For example, large single crystals of synthetic sapphire can be machined to form a surgical contact lens as desired. In general, surgical contact lenses can be made the same sizes and optical configurations presently used for conventional glass lenses. As such, a surgical lens of the present invention can be used in conjunction with lens rings that are currently available for use with conventional glass lenses. Thus, lenses of the invention can be used together with hardware presently used in surgical procedures employing glass lenses.

In FIGS. 2A–2G, cross-sectional side views of various and exemplary surgical contact lens 20a–20g according to the present invention are depicted. By virtue of having a surface that complements an underlying cornea, these depicted lenses are particularly suitable for use by placing directly on a patient's eye as generally depicted in FIG. 1. However, these lenses also may be suitably employed in other aspects of the invention such as in a viewing device as discussed above.

Each of the lenses depicted in FIGS. 2A–2G has a first surface 22 and a second surface 24, which second surface a medical practitioner would took through to a patient's eye (see FIG. 1). In each of the illustrated surgical contact lens 20a–20g, the first surface 22 is configured in a preferred shape whereby the lens complements the geometric shape or curvature of a patient's underlying cornea (see FIG. 1). More particularly, in such preferred shapes, the first lens surface 22 in cross-section has a generally concave shape so as to form a portion of a spherical surface having a radius that corresponds to the radius of curvature of the central anterior cornea of a person's eye. In an exemplary embodiment, the contact radius ($R_1$ see FIG. 2A) for the first surface of a surgical contact lens 20 for adult use will be from about 7.5 to 8.2 mm, more preferably from about 7.8 to about 8.0 mm, which corresponds to the average radius of curvature of the central anterior adult cornea. In other aspects of the invention such as where a lens is employed in a viewing device, the lens first surface need conform to a cornea surface in such manner and may be e.g. substantially flat.

The second surface 24 of the surgical contact lens 20 is suitably configured with any of a wide variety of geometrical arrangements or configurations so as to produce a surgical contact lens having any one of a number of optical viewing configurations.

Figure 2G:
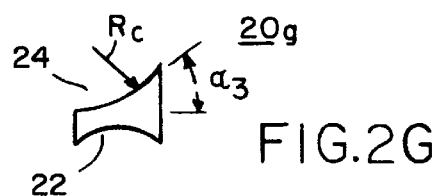
Figure 2C:
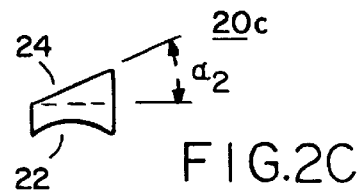
Figure 2F:
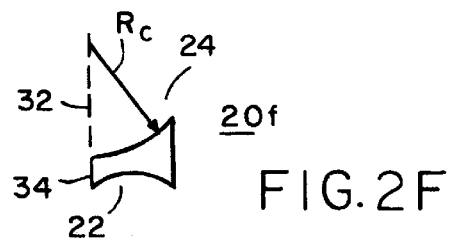
Figure 2B:
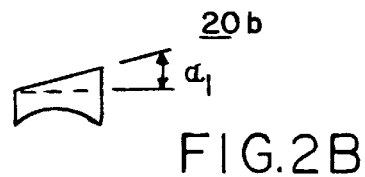
Figure 2E:
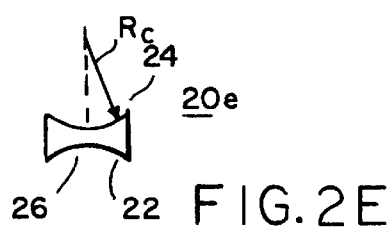
Figure 2A:
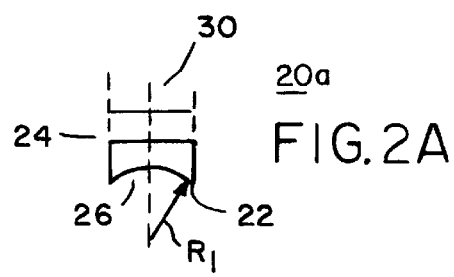

FIG. 2A depicts a surgical contact lens 20a whose second surface 24 is a flat planar surface that is perpendicular to the line 30 passing through the midpoint 26 of the convex first surface 22, to provide a surgical contact lens having a planar/concave configuration.

FIGS. 2B–2C depict a surgical contact lens 20b,c having second surface 24 that is a flat sloping surface at an angle $\alpha$ to provide a surgical contact lens having a prism/concave configuration. In the embodiment shown in FIG. 2B, the angle $\alpha_1$ is 15 degrees forming a 15° prism/concave surgical contact lens 20b, and for the embodiment shown in FIG. 2C the angle $\alpha_2$ is 30 degrees forming a 30° prism/concave surgical contact lens 20c. Although 15 and 30 degree angles are illustrated, the flat sloping second surface 24 suitably may be at any of a number of angles, and preferably flat sloping second surface 24 will be at an angle of from about 10 degrees to about 40 degrees.

FIGS. 2D–2E depict a surgical contact lens 20d,e having second surface 24 in cross section that is a generally concave shape so as to form a portion of a spherical surface having a given radius. Also, the centers of the radii for the first and second surfaces 22,24 are located on the same line, in particular the line 30 passing through the midpoints 26,28 of the first and second concave surfaces, to provide a concave/concave configuration.

In the embodiment shown in FIG. 2D, the radius of curvature ($R_c$) of the second surface 24 is set the same as the radius of curvature ($R_f$) for the first surface 22 and thus forms a symmetric-concave/concave surgical contact lens 20d. For the embodiment shown in FIG. 2E, the radius of curvature ($R_c$) of the second surface 24 is different from the radius of curvature ($R_f$) for the first surface 22 and thus forms an asymmetric-concave/concave surgical contact lens 20e. In a specific embodiment, the second surface radius of curvature ($R_c$) is 10 mm. The second surface radius of curvature preferably will be from about 5 mm to about 20 mm.

FIG. 2F shows a surgical contact lens 20f whose second surface 24 in cross section is a generally concave shape to form a portion of a spherical surface having a given radius. Also, the center of the radius of curvature ($R_c$) for the second surface 24 is offset from the center of the radius of curvature ($R_f$) for the first surface 22, to provide an offset-concave/concave configuration. Additionally, the second surface radius of curvature (Rc) can be set the same as or different from the first surface radius of curvature. In a specific and exemplary embodiment, the second surface radius of curvature ($R_c$) is 12 mm and the center of revolution for the second surface 24 is on a line 32 that extends from an outside vertical side surface 34 of the surgical contact lens 20f (see FIG. 2F). The second surface radius of curvature for such this offset-concave/concave design preferably will be from about 5 mm to about 20 mm.

FIG. 2G depicts a surgical contact lens 20g whose second surface 24 includes a plurality of geometric configurations. In a specific embodiment, as illustrated in FIG. 2G, the second surface 24 includes a flat sloping surface at an angle $\alpha_3$ and a depressed region in a portion of the flat sloping surface that in cross section is generally concave so as to form a portion of a spherical surface having a given radius of curvature ($R_c$). That configuration is prism-concave/concave contact lenses. In an exemplary embodiment, the depressed region radius of curvature is 8 mm and the angle $\alpha_3$ is about 30°.

Although various combinations of a flat sloping surface and spherical depression is illustrated in FIGS. 2A–2G, the second surface of the lenses of the invention may have a wide variety of other geometrical shapes and surfaces that yields a given optical configuration. For example, the second surface suitably may comprise a flat planar surface like that shown in FIG. 2A with a concave groove across a portion of the surface or a spherical depression therein.

Figure 3:
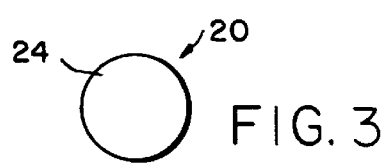
FIG. 3 is a top view of the surgical contact lens of FIG. 1.

As shown in the top view of FIG. 3 surgical contact lenses of the invention preferably have a cylindrical periphery (top view), where the first surface 22 is located at or machined into one end of the cylinder and the second surface is located at or machined into the other end thereof. A cylindrical member is generally preferred to enable use of the surgical contact lenses 20 with lens rings currently available for conventional glass surgical contact lenses. For example, a surgical contact lens of the invention preferably has a diameter (d, see FIG. 2A) of about 11 mm for use with conventional lens rings employed for an adult cornea. However, surgical contact lenses of the invention also may have other peripheral shapes, e.g. a hexagonal or octagonal shaped member, or a member with essentially any other geometric shape having two opposing end surfaces that comprise the first and second lens surfaces 22,24.

Use of such surgical contact lenses of the invention can be further understood from the following discussion with reference to FIGS. 1–3.

In preparation of a surgical procedure, the surgical contact lens 20 is sterilized and cleaned using any of a number of techniques known to those skilled in the art. For example, a cleaned contact lens can be autoclaved to sterilize the lenses for use. In contrast to conventional glass surgical contact lenses, the cleaning and sterilizing procedures can be simplified because special handling procedures or cautions to avoid scratching and other optical degradations are not required.

Before a surgical contact lens is employed in a procedure, a medical practitioner such as an ophthalmic surgeon, typically sutures a lens ring 10 to the eye 2 using any of a number techniques known in the art. The lens ring 10 is positioned on the anterior surface of the eye 2 so it spans the cornea. Also, a transparent material cushion 12 of a material such a Healon is typically placed over the anterior surface of the eye on and about the cornea to prevent corneal abrasion.

The medical practitioner then selects a lens having the desired optical characteristic(s) for viewing the interior of the patient's eye; e.g. the medical practitioner selects a lens design as desired for particular viewing properties. The lens is then typically fitted into a lens ring 10 so the first surface 22 therefor is proximate to and spans the patient's cornea as generally illustrated in FIG. 1. To view the interior surfaces 4 or regions of the patient's eye, the medical practitioner looks through the second surface 24 of the surgical contact lens and thus through the cornea. Typically, as the surgical or ophthalmic procedure progresses, the medical practitioner removes the surgical contact lens from the lens ring and fits another lens therein. Such change of lenses may be done as required to provide a lens that provides the optimum viewing properties.

When the medical procedure is completed, a lens of the invention may be readily re-cleaned and re-sterilized without optical degradation, and then used in additional medical procedures. As discussed, the robust characteristics of lenses of the invention allow procedures to be simplified to eliminate steps or cautions required with prior surgical lenses. Additionally, as discussed above, the excellent optical properties of sapphire allow the surgical contact lenses of the invention to replicate or even surpass (e.g., enhanced angle of view) the optical performance of conventional surgical contact lenses.

Figure 4:
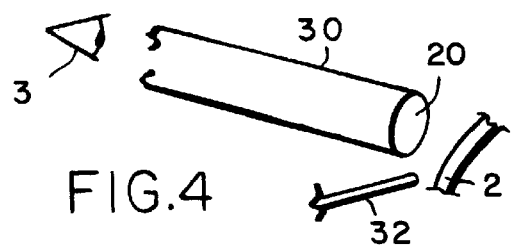
FIG. 4 depicts a surgical viewing device that incorporates a lens of the invention.

FIG. 4 of the drawings depicts another preferred aspect of the invention wherein a sapphire lens 20 of the invention is attached permanently or releasably to viewing device 30 through which medical practitioner 3 can view patient's eye 2. Device 30 suitably can be hand-held either by the primary surgeon 3, or more typically by another assisting medical personnel. With this system, patient's eye 2 may be irrigated as desired during the course of a surgical procedure, e.g. via infusion line 32 which delivers a suitable buffered or other solution to eye 2 as desired.

Figure 5A:
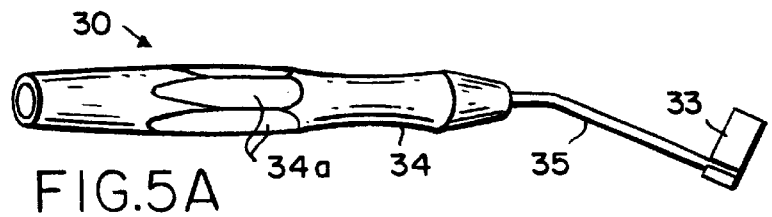
FIGS. 5A, 5B and 5C depict a preferred viewing device for use with a lens of the invention.
Figure 5B:
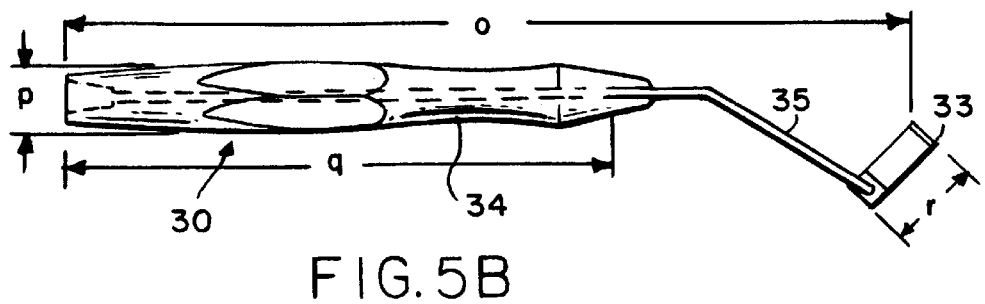
Figure 5C:
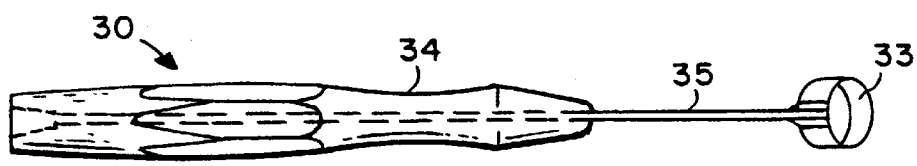

FIGS. 5A, 5B and 5C depict a preferred viewing device 30 wherein a sapphire lens of the invention can be releasably or permanently mounted in lens holder 33. Typically, a lens of the invention will be releasably fitted within holder 33 to enable cleaning of the lens as desired. This preferred device includes handle 34 with topography 34a to facilitate handling of the device during a medical procedure. The device preferably has an arcuate forward handle 35 to facilitate viewing of a patient's eye. This device may be of a variety of dimensions. A preferred device has an overall length (length o shown in FIG. 5B) of about 5.2685 inches: a handle 34 width (width p as shown in FIG. 5B) of about 0.375 inches; a primary handle length (length q as shown in FIG. 5B) of 3.4 inches; and a lens holder width (width r as shown in FIG. 5B) of 0.5704 inches.

Figure 6:
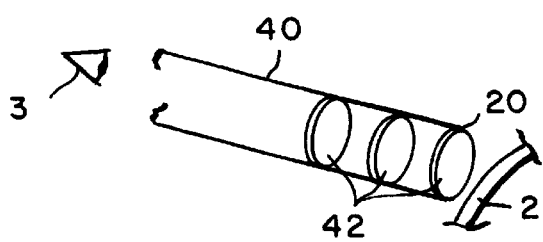
FIG. 6 depicts a multiple lens surgical viewing device that incorporates a lens of the invention.

FIG. 6 of the drawings shows view in a device 40 which has multiple lenses 42 and includes one or more sapphire lenses 20 of the invention. Such a multiple lens system is often used to provide a wide angle viewing and generally will be a hand-held device, manipulated either by the primary physician 3 or more frequently another assisting person. Device 40 may suitably contain a single sapphire lens of the invention, or more typically the device will contain a plurality of sapphire lens of the invention.

The invention also includes kits that comprise one or more surgical contact lenses of the invention, preferably packaged in sterile condition. Kits of the invention also may be include a viewing device for use with a sapphire lens, e.g. such as a device shown in FIGS. 4 or 5, one or more lens rings 10, preferably packaged in sterile condition, and/or written instructions for use of the lens and other components of the kit.

The foregoing description of the invention is merely illustrative thereof, and it is understood that variations and modifications may be made without departing from the spirit or scope of the following claims.

What is claimed is:

1. A surgical contact lens, used to view interior structures and regions of an eye, comprising:
   a transparent member that comprises sapphire, the transparent member having a first surface, a second surface, and an optical characteristic determined by respective configurations of the first and second surfaces for viewing a posterior region of the eye.

2. The surgical contact lens of claim 1 wherein at least about 50% of the total volume of the transparent member is sapphire.

3. The surgical contact lens of claim 1 wherein at least about 90% of the total volume of the transparent member is sapphire.

4. The surgical contact lens of claim 1 wherein the transparent member comprises a glass body that is encapsulated by sapphire.

5. The surgical contact lens of claim 1 wherein the transparent member is completely formed from sapphire.

6. The surgical contact lens of claim 1 wherein the transparent member formed is from a single crystal of sapphire.

7. The surgical contact lens of claim 1 wherein the transparent member has a first surface and a second surface,
   the first surface having a shape that complements a cornea's curvature; and
   the second surface having a shape that, in cooperation with the first surface shape, provides an optical configuration suitable for viewing the interior of the eye.

8. The surgical contact lens of claim 7 wherein the first surface shape is concave and the second surface shape is offset concave, prism-concave, asymmetric concave, symmetric concave, prism or a planar geometric configuration.

9. The surgical contact lens of claim 1 wherein the thickness of the transparent member between the first and second surfaces is about 2 mm or less.

10. The surgical contact lens of claim 1 wherein the transparent member is configured to complement a lens ring.

11. A method for viewing the interior of an eye, comprising:
   (a) providing a surgical contact lens of claim 1; and
   (b) removably disposing the surgical contact lens on the eye so that the first surface is proximate to the cornea and a user looking through the second surface can view the posterior region of the eye interior.

12. The method of claim 11 wherein a lens ring is sutured to the eye and the contact lens is removably fitted in the lens ring.

13. The method of claim 11 wherein a plurality of the surgical contact lenses are provided with each surgical contact lens of the plurality having a different surface geometry; and one of the plurality of the surgical contact lenses is selected for viewing the eye interior.

14. A method for viewing the interior of an eye, comprising:
   (a) providing a surgical contact lens of claim 1; and
   (b) viewing through the lens the posterior region of a patient's eye.

15. The method of claim 14 wherein the lens is mounted in a viewing device.

16. The method of claim 14 wherein the eye is infused with a solution while being viewed.

17. The method of claim 15 wherein the viewing device is held by a medical personnel while the eye is being viewed.

18. The method of claim 15 wherein the lens is mounted in a multiple lens device.

19. A method for making a solid sapphire surgical contact lens, comprising:

machining a block of sapphire to yield a member having at least a first surface and a second surface, wherein the first surface is configured with a geometry that complements the radius of curvature of a cornea, and wherein the second surface is configured to have a geometry that, in cooperation with the first surface geometry, yields a given optical configuration; and polishing the member to yield a sapphire surgical contact lens having a desired optical characteristic for viewing a posterior region of a patient's eye.

20. The method of claim 19 wherein the second surface is machined so it is one of an offset-concave, a prism-concave, an a symmetric-concave, a symmetric-concave, a prism or planar geometric configuration.

21. The method of claim 19, wherein the block of sapphire comprises a single crystal of sapphire.

22. The method of claim 19 wherein the sapphire block is machined to provide a thickness of the member between the first and second surfaces of about 2 mm or less.

23. A medical device kit, comprising one or more of the surgical contact lenses of claim 1.

24. The kit of claim 23 wherein the one or more lenses are packaged in sterile condition.

* * * * *